(12) United States Patent
Jones

(10) Patent No.: US 8,517,992 B2
(45) Date of Patent: Aug. 27, 2013

(54) DRIVE MECHANISM FOR AN INJECTION DEVICE AND AN INJECTION DEVICE WITH SUCH A DRIVE MECHANISM

(75) Inventor: Christopher Jones, Tewkesbury (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/384,049

(22) PCT Filed: Jul. 14, 2010

(86) PCT No.: PCT/EP2010/060127
§ 371 (c)(1),
(2), (4) Date: May 15, 2012

(87) PCT Pub. No.: WO2011/006925
PCT Pub. Date: Jan. 20, 2011

(65) Prior Publication Data
US 2012/0220941 A1 Aug. 30, 2012

(30) Foreign Application Priority Data
Jul. 15, 2009 (EP) ..................................... 09009214

(51) Int. Cl.
*A61M 5/315* (2006.01)
*A61M 5/20* (2006.01)

(52) U.S. Cl.
USPC ............ 604/154; 604/211; 604/155; 600/432

(58) Field of Classification Search
USPC ................... 604/67, 151–152, 154–156, 224, 604/207–208, 209–211; 600/432
See application file for complete search history.

(56) References Cited

U.S. PATENT DOCUMENTS

| 4,498,904 A * | 2/1985 | Turner et al. .................. 604/211 |
| 6,235,004 B1 * | 5/2001 | Steenfeldt-Jensen et al. ............................. 604/207 |

(Continued)

FOREIGN PATENT DOCUMENTS

| EP | 0567186 | 10/1993 |
| WO | 99/38554 | 8/1999 |

(Continued)

OTHER PUBLICATIONS

International Search Report for International App. No. PCT/EP2010/060127, completed Aug. 10, 2010.
International Preliminary Report on Patentability for Int. App. No. PCT/EP2010/060127, issued Jan. 17, 2012.

*Primary Examiner* — Quynh-Nhu H Vu
(74) *Attorney, Agent, or Firm* — McDonnell Boehnen Hulbert & Berghoff LLP

(57) ABSTRACT

A drive mechanism for an injection device in which a piston is successively moved in a first axial direction in relation to a medicament cartridge containing a medicament selectively to drive a bung closing a first end of the medicament cartridge into the medicament cartridge to expel medicament through a delivery member located at a second end of the medicament cartridge, the drive mechanism comprising: a base member, a first drive member fixed relative to the base member, a second drive member axially and rotatably moveable relative to the first drive member and a piston member axially moveable relative to the first and second drive member, wherein the second drive member is drivingly connected between the first drive member and the piston member such that rotation of the second drive member in a first direction of rotation relative to the first drive member and the piston member causes the second drive member to move in the first axial direction relative to the first drive member and the piston member to move in the first axial direction relative to both the first and second drive member, and an injection device comprising such a drive mechanism.

15 Claims, 1 Drawing Sheet

(56) References Cited

U.S. PATENT DOCUMENTS

| | | | |
|---|---|---|---|
| 6,248,093 B1* | 6/2001 | Moberg | 604/131 |
| 7,771,400 B2* | 8/2010 | Nielsen | 604/211 |
| 8,012,131 B2* | 9/2011 | Moser et al. | 604/208 |
| 2002/0032402 A1* | 3/2002 | Daoud et al. | 604/26 |
| 2005/0020980 A1* | 1/2005 | Inoue et al. | 604/152 |
| 2008/0108953 A1* | 5/2008 | Moser et al. | 604/224 |

FOREIGN PATENT DOCUMENTS

| | | |
|---|---|---|
| WO | 01/10484 | 2/2001 |
| WO | 01/87384 | 11/2001 |
| WO | 2006/078817 | 7/2006 |

* cited by examiner

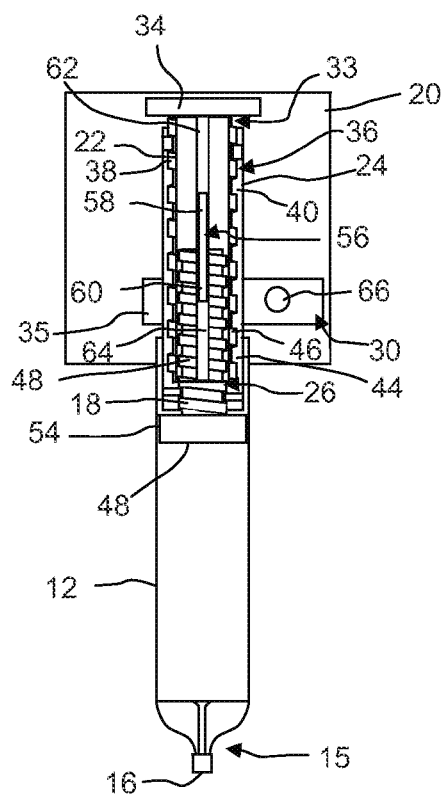
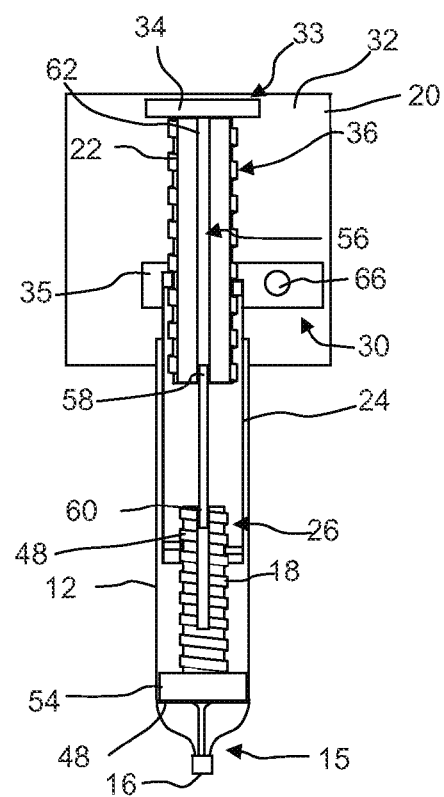
Figure 1
Figure 2

DRIVE MECHANISM FOR AN INJECTION DEVICE AND AN INJECTION DEVICE WITH SUCH A DRIVE MECHANISM

CROSS REFERENCE TO RELATED APPLICATIONS

The present application is a U.S. National Phase Application pursuant to 35 U.S.C. §371 of International Application No. PCT/EP2010/060127 filed Jul. 14, 2010, which claims priority to European Patent Application No. 09009214.9 filed on Jul. 15, 2009. The entire disclosure contents of these applications are herewith incorporated by reference into the present application.

FIELD OF INVENTION

The present invention relates to a drive mechanism for an injection device and an injection device with such a drive mechanism.

In particular the present invention relates to improvements in a drive mechanism for a portable injection device for dispensing controlled quantities of a medicament. The invention also relates to an injection device incorporating the improved drive mechanism.

BACKGROUND

Injection devices are known for the self administration of a medicament by patients. For example, those suffering from diabetes may require regular injections of insulin, others may require regular injections of a growth hormone. Injection devices allow the patient to select a dose and to administer that dose. It is known to automate this process so that a user need only press a button and the injection device will dispense a selected dose of medicament. This relieves the patient of the task of controlling the amount dispensed while manually expelling the medicament from the injection device. This is a particular problem for the elderly, the infirm, those suffering from vision difficulties and those suffering from diabetes related problems which impair their faculties.

The medicament is typically contained within a cartridge located within the injection device. The cartridge has a bung or piston at one end which is driven towards a second end of the cartridge to expel the medicament for the injection device. It is a problem that injection devices should be small enough to fit into a jacket pocket or a hand bag without difficulty. At the same time, the injection device must be of a size that enables a piston or the like used to drive the cartridge and to be fully withdrawn from the cartridge to allow for replacement of the cartridge.

The object of the invention is to provide a drive mechanism for an injection device and an injection device with such a drive mechanism by which these conflicting requirements are fulfilled.

SUMMARY

According to a first aspect of the present invention, there is provided a drive mechanism for an injection device in which a piston is successively moved in a first axial direction in relation to a medicament cartridge containing a medicament selectively to drive a bung closing a first end of the medicament cartridge into the medicament cartridge to expel medicament through a delivery member located at a second end of the medicament cartridge, the drive mechanism comprising a base member, a first drive member fixed relative to the base member, a second drive member axially and rotatably moveable relative to the first drive member and a piston member axially moveable relative to the first and second drive members, characterised in that the second drive member is drivingly connected between the first drive member and the piston member such that rotation of the second drive member in a first direction of rotation relative to the first drive member and the piston member causes the second drive member to move in the first axial direction relative to the first drive member and the piston member to move in the first axial direction relative to both the first and second drive members.

Preferably, the second drive member is in screw threaded engagement with the first drive member and the piston member. More preferably, the second drive member comprises a generally annular sleeve member, the sleeve member having a first internal thread for engagement with a corresponding thread on the first drive member, and a second internal thread for engagement with a corresponding thread on the piston member. Advantageously, the first drive member comprises a first axially extending elongate spigot portion having a thread formed about an external surface for engagement with the corresponding first internal thread of the second drive member, and the piston member comprises a piston head and an axially extending piston rod having a thread formed about an external surface for engagement with the corresponding second internal thread of the second drive member.

In a particularly preferred embodiment, the first drive member and the piston member each have an axially extending bore, the mechanism further comprising a support member having a first portion adapted to slidingly engage with the bore of the first drive member and a second portion adapted to slidingly engage with the bore of the piston member, the arrangement being such that the support member prevents the piston member from rotating relative to the first drive member. More preferably, the arrangement is adapted such that when the drive mechanism is fully retracted, the spigot portion of the first drive member is substantially entirely received within the second drive member, and the piston rod is substantially entirely received within the internal bore of the first drive member.

Preferably, the first drive member can be formed as an integral component with the base member.

Preferably, the drive mechanism further comprises drive means for selectively rotating the second drive member in at least the first direction of rotation.

More preferably, the drive means for selectively rotating second drive member comprises an electric motor arranged to drive the second drive member in at least the first direction of rotation.

A plurality of elongate splines may be provided on a surface on the second drive member and the electric motor may be adapted to drive the second drive member through the splines.

Preferably, the electric motor drives the second drive member through one or more gears. In one preferred embodiment, the electric motor drives the second drive member by means of a worm gear which engages with the splines. Alternatively, the electric motor drives the second drive member by means of a spur gear which engages with the splines.

Preferably, the drive mechanism further comprises an electronic control device for controlling the operation of the drive mechanism so as to regulate delivery of the medicament in use.

In accordance with a second aspect of the invention, there is provided an injection device comprising a drive mechanism in accordance with the first aspect of the invention.

The invention will now be described, by way of example only, with reference to the accompanying drawings.

BRIEF DESCRIPTION OF THE FIGURES

FIG. 1 shows a schematic plan view of a part of an injection device including a drive mechanism according to a first embodiment of the present invention and a medicament cartridge, in which the drive mechanism is fully retracted and a medicament cartridge is full;

FIG. 2 is a plan view of the injection device of FIG. 1, showing the drive mechanism fully extended and the medicament cartridge empty.

DETAILED DESCRIPTION

Like reference numerals will be used to refer to like parts of the injection device.

Referring first to FIGS. 1 to 2, there may be seen part of an injection device comprising a drive mechanism in accordance with a first embodiment of the present invention, indicated generally at 10, and a medicament cartridge 12.

For the sake of clarity, the medicament cartridge is shown as being transparent in all the drawings so that details of the drive mechanism can be seen within the cartridge. It will be understood that in practice the medicament cartridge may not be transparent.

Although not shown, those skilled in the art will appreciate that the injection device will comprise a main housing and a needle unit including a delivery member in the form of a hollow needle which can be secured to a first end of the main housing. A medicament cartridge 12 having a first end 14 and a second end 15 may be stored in the main housing. When the needle unit is in place, the needle unit pierces a flexible membrane 16 at the second end 15 of the medicament cartridge 12. A displaceable bung 18 is located at the first end of the medicament cartridge 12 when the cartridge is full as shown in FIG. 1. A cover (also not shown) may be provided over the first end of the main housing to protect the needle unit from damage and a user from inadvertent pricking by the needle. The cover also provides a discrete appearance for the injection device.

The drive mechanism comprises a base member 20, a first drive member 22, a second drive member 24, a piston member 26, a control device (indicated schematically at 28 in FIG. 2), and a drive means, indicated generally at 30. The base member 20 may form part of the main housing of the injection device and has a planar portion 32, a mounting tab 34 projecting from the planar portion 32 for supporting one end of the first drive member 22 and an annular guide 35 for slidingly supporting the second drive member 24.

The first drive member 22 has a mounting portion 33 at one end which can be attached to the mounting tab 34 of the base member such that the first drive member is fixed both axially and rotationally relative to the base member. The first drive member also has a spigot portion 36 that extends axially from the mounting portion 33 towards the medicament cartridge. A screw thread 38 is formed on the outer surface of the spigot portion 36 over most of its length.

The second drive member 24 is in the form of a generally annular sleeve and has a first bore portion 40 that extends over the majority of its length. A first internal screw thread (not shown) is formed on the surface of the first bore portion for engagement with the thread 38 on the outer surface of the spigot portion 36 of the first drive member 22. The arrangement is such that rotation of the second drive member 24 results in the second drive member advancing axially relative to the first drive member towards the second end 15 of the medicament cartridge 12 along the thread 38.

The end of the second drive member 24 closest to the medicament cartridge 12 is partially closed off by means of a wall 42 in which is formed a second bore portion 44 of smaller diameter than the first bore portion 40. A second internal thread (also not shown) is formed on the surface of the second bore portion 44 for engagement with a corresponding thread 46 formed on a piston rod 48 of the piston member 26. The screw thread 46 on the piston rod 48 and the second internal thread in the second bore portion 44 of the second drive member are arranged such that rotation of the second drive member relative to the piston member results in the piston member 26 advancing axially towards the second end 15 of medicament cartridge relative to the second drive member 24.

It should be noted that the thread 38 on the spigot portion 36 of the first drive member 22 and the thread 46 on the piston rod 48 are of opposite hand.

The outer surface of the second drive member 24 is slidingly received within the annular guide 35 of the base member which acts to support the second drive member 24 and to guide its movement in the axial direction. A plurality of axial splines are provided on the outer surface of the second drive member for engagement with a worm gear that forms part of the drive means 30 for rotating the second drive member as will be described in more detail below.

The piston member 26 comprises a piston head 54 which can be received within the medicament cartridge 12 for contact with the bung 18. The piston rod 48 extends axially away from the piston head 54 towards the first drive member 22 and is in screw threaded engagement with the second bore portion 44 of the second drive member 24 as has been described above.

An elongate support member 56 interconnects the first drive member and the piston member and has a first, relatively short portion 58 and a second, relatively long portion 60. The first portion 58 is dimensioned so as to be slidingly received within a bore 62 formed in the spigot portion 36 of the first drive member 22. The second portion 60 of the support member 56 is dimensioned so as to be slidingly received within a bore 64 formed in the piston rod 48. The profiles of the first portion 58 of the support member and the bore 62 in the first drive member are selected so that the support member 56 cannot rotate relative to the first drive member 22. Similarly, the outer profile of the second portion 60 of the support member 56 and the bore 64 in the piston rod are selected so that the piston member 26 cannot rotate relative to the support member 56. Thus the support member 56 acts as an internal key for preventing the piston member 26 from rotating relative to the first drive member 22 when the second drive member 24 is rotated.

The bore 62 in the first drive member and the piston rod 48 are sized so that the piston rod 48 can be received within the bore 62 when the drive mechanism is fully retracted.

Rotation of the second drive member 24 is carried out by the drive means 30. The drive means 30 comprises an electric motor 66, a gear train indicated generally at 68, a control device (not shown in the figures), and a power source in the form of a battery which provides power for the motor 66 and the control device by means of cables (not shown).

The electric motor 66 is mounted to the base member 20 adjacent to the second drive member 24 and with the axis of its output shaft arranged generally perpendicular to the axis of rotation of the second drive member 24. Drive is transmitted from the electric motor 66 to the second drive member by means of the gear train 68 which includes a first, relatively small gearwheel mounted to the output shaft of the electric motor 66, a second, relatively large gear wheel in mesh with the first gearwheel, and the worm: gear which is mounted for rotation with the second gear wheel. The worm gear is supported for rotation about an axis that is generally parallel to the axis of rotation of the output shaft of the electric motor 66 by means of a pair of flanges projecting from the annular guide 35 of the base member 20. To this end the worm gear has a spigot portion at either end, each spigot portion being received in a hole in a respective one of the flanges. The worm gear engages with the splines on the second drive member 24 through an opening in the wall of he annular guide 35.

Part of the second gear wheel is accommodated in a recess provided in the base of the annular guide 35, to enable the worm gear to be positioned adjacent the second drive member 24. It will also be noted that the second drive member 24 effectively forms the final gear in the gear train.

It can be seen that rotation of tile output shaft of the motor 66 in a first direction will be transmitted via the first gear wheel, the second gearwheel, the worm gear and the splines to cause the second drive member 24 to rotate relative to the first drive member 22 in the direction of arrow A in FIG. 3. Rotation of the second drive member 24 results in the second drive member 24 advancing axially or linearly towards the second end 15 of the medicament cartridge along the thread 38 on spigot portion 36 of the first drive member 22 and will simultaneously cause the piston member 26 to advance axially towards the second end 15 of medicament cartridge relative to both the second drive member 24 and the first drive member 22.

As the piston member 26 is advanced axially towards the second end 15 of the medicament cartridge, the piston head 54 contacts the bung 18 to move the bung towards the second end of the medicament cartridge to expel medicament. By appropriate control of the electric motor 66, the piston member 26 can be caused to advance towards the second end 15 of the medicament cartridge by a predetermined amount in order to expel a predetermined dose of medicament in a controlled manner.

Rotation of the output shaft of the motor 66 in a second direction opposite to the first will result in the second drive member 24 being rotated relative to the first drive member 22 in an opposite direction. This will cause the piston member 26 and the second drive member 24 to be moved axially away from the second end 15 of the medicament cartridge, thus retracting the drive mechanism. Operation of the electric motor, and hence movement of the second drive member 24 and the piston member 26 is controlled by the control device 28. The device 28 may include a microprocessor (not shown) and a user interface having a display through which information can be displayed to the user and input means by which a user can input instructions, for example to set a required dose of the medicament (also not shown).

Operation of the injection device will now be described.

In FIG. 1 the injection device is shown with a medicament cartridge 12 in position. The medicament cartridge 12 is full, so that the bung 18 is positioned close to the first end 14 of the cartridge and the drive mechanism is fully retracted. In this position, the spigot portion 36 of the first drive member is almost fully received within the second drive member 24 and the piston rod 48 is almost fully received within the bore 62 of the first drive member and the support member 56 is accommodated within the bores 62, 64 of the first drive member and the piston rod 48, respectively.

When a user wishes to administer a dose of medicament, he prepares the injection device as required and activates the control device which will display various information on the user display, such as the amount of medicament available in the cartridge, for example. The user can then use the input means to set a required dose of medicament. In accordance with a preset algorithm, the control device determines the length of time the motor 66 must be operated in the first direction in order to move the piston member axially towards the second end 15 of the cartridge by an amount that will deliver the required dose. Once the user has indicated that he is ready for the dose to be administered, the control device effects delivery by activating the electric motor for the required amount of time.

The above sequence can be repeated a number of times to administer medicament to a user until the medicament cartridge is empty or until it has insufficient medicament to deliver a predetermined minimum dose. At this stage, the drive mechanism will be fully extended in the maximum dispense position as shown in FIG. 2. In order to reset the drive mechanism 10 and to enable replacement of tile medicament cartridge, the electric motor 66 is operated in the reverse direction to move the piston member 26 and the second drive member 24 axially in a direction away from the second end 15 of the medicament cartridge 12 until the drive mechanism is fully retracted as shown in FIG. 1. This can be done in response to an input from a user or automatically by the control device when it detects that the medicament cartridge 12 is empty or has insufficient medicament to deliver the predetermined minimum dose. The empty medicament cartridge 12 can then be removed and replaced by a new cartridge.

An alternative embodiment of a drive mechanism 10 in accordance with invention is now described with reference to FIGS. 1 and 2. The same reference numerals will be used to denote parts which have similar functions in the drive mechanism 10.

The main differences are:

the spigot portion 36 of the first drive member 22 is formed as an integral part of the base member 20;

the annular guide 35 is also formed as an integral part with the spigot portion 36 of the first drive member;

an alternative drive means 30 is used to rotate the second drive member.

In the drive mechanism 10 the spigot portion 36 of the first drive member is formed integrally with the mounting tab 34 on the base member 20. Also formed integrally with the tab 34 and surrounding the spigot portion 36 is the annular guide 35. The annular guide 35 is spaced from the spigot portion 36 so that the second drive member 24 can be slidingly received in a gap formed between the annular guide 35 and the spigot portion 36.

The drive means 30 comprises an electric motor 66 which is mounted to the base member 20 such that the axis of rotation of an output shaft of the motor is substantially parallel with the axis of rotation of the second drive member 24. Drive is transmitted from the electric motor to the second drive member 24 via a series of spur gears. Whilst most of the spur gears in the series have their axes of rotation aligned substantially parallel with the axis of rotation of the second drive member 24, it will be noted that the axis of rotation of the final spur gear 90 in the series is arranged at an angle to the axis of rotation of the second drive member 24. The final spur gear also has a spigot that is rotatably supported in a hole in a flange projecting from one side of the annular guide 35.

Apart from the differences discussed above, the drive mechanism 10 is constructed and operates in the same manner as the guide mechanism 10 described above in relation to FIGS. 1 to 2.

It will be seen that the inventive drive arrangement is very compact when fully retracted but is capable of being extended so as to move the bung 18 to the maximum dispense position. Furthermore, in accordance with the preferred embodiments, an internal key or support member 56 can be used to prevent the piston member 26 from rotating. This arrangement is simpler than that used in known telescopic, threaded drive mechanisms for injection devices in which additional external sleeves are used to prevent the piston member or other components from rotating.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬ decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A drive mechanism for an injection device in which a piston is successively moved in a first axial direction in relation to a medicament cartridge containing a medicament selectively to drive a bung closing a first end of the medicament cartridge into the medicament cartridge to expel medicament through a delivery member located at a second end of the medicament cartridge, the drive mechanism comprising:
   a base member,
   a first drive member fixed relative to the base member,
   a second drive member axially and rotatably moveable relative to the first drive member and a piston member axially moveable relative to the first and second drive member,
   characterised in that
   the second drive member is drivingly connected between the first drive member and the piston member such that rotation of the second drive member in a first direction of rotation relative to the first drive member and the piston member causes the second drive member to move in the first axial direction relative to the first drive member and the piston member to move in the first axial direction relative to both the first and second drive member.

2. A drive mechanism as claimed in claim 1, in which the second drive member is in screw threaded engagement with the first drive member and the piston member.

3. A drive mechanism as claimed in claim 2, in which the second drive member comprises a generally annular sleeve member, the sleeve member having a first internal thread for engagement with a corresponding thread on the first drive member, and a second internal thread for engagement with a corresponding thread on the piston member.

4. A drive mechanism as claimed in claim 3, in which the first drive member comprises a first axially extending elongate spigot portion having a thread formed about an external surface for engagement with the corresponding first internal thread of the second drive member, and the piston member comprises a piston head and an axially extending piston rod having a thread formed about an external surface for engagement with the corresponding second internal thread of the second drive member.

5. A drive mechanism as claimed in claim 4, in which the first drive member and the piston member each have an axially extending bore, the mechanism further comprising a support member having a first portion adapted to slidingly engage with the bore of the first drive member and a second portion adapted to slidingly engage with the bore of the piston member, the arrangement being such that the support member prevents the piston member from rotating relative to the first drive member.

6. A drive mechanism as claimed in claim 5, the arrangement being adapted such that when the drive mechanism is fully retracted, the spigot portion of the first drive member is substantially entirely received within the second drive member, and the piston rod is substantially entirely received within the internal bore of the first drive member.

7. A drive mechanism as claimed in claim 1, in which the first drive member is formed as an integral component with the base member.

8. A drive mechanism as claimed in claim 1, further comprising drive means for selectively rotating the second drive member in at least the first direction of rotation.

9. A drive mechanism as claimed in claim 8, the drive means for selectively rotating the second drive member comprises an electric motor arranged to drive the second drive member in at least the first direction of rotation.

10. A drive mechanism as claimed in claim 9, in which a plurality of elongate splines are provided on a surface of the second drive member and the electric motor is adapted to drive the second drive member through the splines.

11. A drive mechanism as claimed in claim 10, in which the electric motor drives the second drive member through on ore more gears.

12. A drive mechanism as claimed in claim 11, in which the electric motor drives the second drive member by means of a worm gear which engages with the splines.

13. A drive mechanism as claimed in claim 11, in which the electric motor drives the second drive member by means of a spur gear which engages with the splines.

14. A drive mechanism as claimed in claim 1, further comprising an electronic control device for controlling the operation of the drive mechanism so as to regulate delivery of the medicament in use.

15. An injection device comprising a drive mechanism in accordance with claim 1.

* * * * *